(12) United States Patent
Sirmans et al.

(10) Patent No.: US 12,419,498 B2
(45) Date of Patent: Sep. 23, 2025

(54) ALL-PURPOSE FOREIGN OBJECT DEBRIS DETECTION AND RETRIEVAL DEVICE

(71) Applicant: Lockheed Martin Corporation, Bethesda, MD (US)

(72) Inventors: Joseph David Sirmans, Marietta, GA (US); Jonathan Richard Olson, Fort Worth, TX (US); Anthony Robert Mann, Fort Worth, TX (US); Gene McGarry, Huntington, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 1017 days.

(21) Appl. No.: 16/938,356

(22) Filed: Jul. 24, 2020

(65) Prior Publication Data

US 2022/0024605 A1  Jan. 27, 2022

(51) Int. Cl.
*B64F 5/60* (2017.01)
*A61B 1/00* (2006.01)
*B64F 5/40* (2017.01)
*G01B 5/00* (2006.01)
*H04N 23/50* (2023.01)

(52) U.S. Cl.
CPC ............ *A61B 1/00133* (2013.01); *B64F 5/40* (2017.01); *B64F 5/60* (2017.01); *G01B 5/0002* (2013.01); *F05D 2230/72* (2013.01); *H04N 23/555* (2023.01)

(58) Field of Classification Search
None
See application file for complete search history.

(56) References Cited

U.S. PATENT DOCUMENTS

| | | |
|---|---|---|
| 4,530,568 A | 7/1985 | Haduch et al. |
| 4,735,501 A | 4/1988 | Ginsburgh et al. |

(Continued)

FOREIGN PATENT DOCUMENTS

| | | |
|---|---|---|
| CA | 2118339 | 4/1995 |
| DE | 102015225445 A1 | 12/2015 |

(Continued)

OTHER PUBLICATIONS

European Patent Office Communication, partial European search report, Application No. 21186476.4-1010, Dec. 10, 2021.

(Continued)

*Primary Examiner* — Lorne E Meade
*Assistant Examiner* — Marc Amar
(74) *Attorney, Agent, or Firm* — Baker Botts L.L.P.

(57) ABSTRACT

In one embodiment, systems and methods include using an inspection system to remove or seal foreign object debris. An inspection system comprises a borescope; wherein a plurality of optical fibers is disposed within the borescope; a mounting system; an articulation system; and a controller, wherein the controller comprises a display; wherein a proximal end of the borescope is coupled to the mounting system, wherein the mounting system is configured to secure the inspection system to an external surface, wherein the mounting system is coupled to the articulation system, wherein the articulation system is configured to actuate the borescope, wherein the articulation system is communicatively coupled to the controller.

3 Claims, 4 Drawing Sheets

(56) References Cited

U.S. PATENT DOCUMENTS

| | | | | |
|---|---|---|---|---|
| 4,784,463 | A * | 11/1988 | Miyazaki | G02B 23/2476 356/241.6 |
| 4,872,446 | A * | 10/1989 | Murata | A61B 5/1076 600/109 |
| 5,311,639 | A * | 5/1994 | Boshier | G02B 23/26 15/324 |
| 5,644,394 | A * | 7/1997 | Owens | F01D 5/005 356/241.5 |
| 5,815,640 | A * | 9/1998 | Wang | B60R 21/0132 700/251 |
| 6,126,591 | A | 10/2000 | McGarry et al. | |
| 7,064,309 | B2 * | 6/2006 | Wagoner | B64F 5/60 250/203.1 |
| 7,422,559 | B2 | 9/2008 | Kehoskie et al. | |
| 8,039,773 | B2 | 10/2011 | Spallek et al. | |
| 9,329,377 | B2 | 5/2016 | Kell et al. | |
| 9,403,244 | B2 * | 8/2016 | Rautenberg | F01D 21/003 |
| 9,955,088 | B2 | 4/2018 | Motzer et al. | |
| 10,544,676 | B2 | 1/2020 | Roberts et al. | |
| 2003/0189178 | A1 * | 10/2003 | Wagoner | B64F 5/30 250/459.1 |
| 2005/0096497 | A1 * | 5/2005 | Gerber | A61F 2/0036 604/60 |
| 2005/0119527 | A1 * | 6/2005 | Banik | A61B 1/00066 600/117 |
| 2005/0235493 | A1 * | 10/2005 | Philip | C23C 4/02 29/889.1 |
| 2006/0042083 | A1 | 3/2006 | Baker et al. | |
| 2007/0171406 | A1 * | 7/2007 | Stokes | F01D 17/02 356/241.1 |
| 2008/0233278 | A1 * | 9/2008 | Hopkins | C23C 24/08 427/142 |
| 2008/0255550 | A1 * | 10/2008 | Bell | A61B 18/04 604/113 |
| 2009/0001059 | A1 * | 1/2009 | Spallek | G02B 23/2469 219/121.64 |
| 2009/0288529 | A1 * | 11/2009 | Floyd | B64F 5/40 83/13 |
| 2013/0199040 | A1 | 8/2013 | Dudeck et al. | |
| 2014/0063228 | A1 | 3/2014 | Boles et al. | |
| 2015/0305597 | A1 * | 10/2015 | Ito | A61B 1/00042 600/117 |
| 2016/0022253 | A1 * | 1/2016 | Khanchandani | A61B 17/00491 606/214 |
| 2018/0042455 | A1 * | 2/2018 | Okamoto | A61B 1/00148 |
| 2018/0264247 | A1 * | 9/2018 | Mantri | A61N 5/1007 |
| 2019/0239726 | A1 * | 8/2019 | Hiraoka | A61B 1/01 |
| 2019/0383158 | A1 * | 12/2019 | Diwinsky | F23N 5/003 |
| 2020/0011181 | A1 * | 1/2020 | Roberts | F01D 5/12 |
| 2021/0022594 | A1 * | 1/2021 | Jen | A61F 2/9517 |
| 2021/0100429 | A1 * | 4/2021 | Chu | A61M 25/0147 |
| 2021/0239010 | A1 * | 8/2021 | Graham | F01D 5/005 |
| 2023/0118392 | A1 * | 4/2023 | Berlin | A61F 9/00781 600/108 |

FOREIGN PATENT DOCUMENTS

| | | | | |
|---|---|---|---|---|
| EP | 0 653 922 B1 | 12/1999 | | |
| FR | 3001401 A1 | 2/2015 | | |
| JP | 1998332599 A | 12/1998 | | |
| JP | 2012115521 A | 6/2012 | | |
| JP | 2015500690 A | 1/2015 | | |
| JP | 2016508222 A | 3/2016 | | |
| JP | 2016118541 A | 6/2016 | | |
| WO | WO-2016076704 A1 * | 5/2016 | | B64F 5/0045 |
| WO | WO 2018/222174 A1 | 12/2018 | | |
| WO | WO2020096892 A1 | 5/2020 | | |

OTHER PUBLICATIONS

Jacob Buckwalter, et al., "*FOD Removal*," Lockheed Martin (24 pages), Apr. 30, 2018.

European Patent Office Communication, extended European search report, Application No. 21186476.4-1010, Apr. 11, 2022.

European Examination Report corresponding to European Application No. 21186476.4, dated Feb. 5, 2024, 6 pages.

Japanese Office Action corresponding to Japanese Patent Application No. 2021-120347 (with English Abstract), dated May 12, 2025, 8 pages.

* cited by examiner

ALL-PURPOSE FOREIGN OBJECT DEBRIS DETECTION AND RETRIEVAL DEVICE

TECHNICAL FIELD

This disclosure generally relates to inspection devices, and more specifically, to an inspection system for detecting and addressing debris present in an aircraft.

BACKGROUND

Foreign object debris (FOD) is a concern on every aircraft. If left undetected and present within an aircraft, it can cause severe damage. There are often hard-to-reach areas present in the airframe where FOD can be located during production or maintenance of each aircraft. Current methods to detect and address FOD involve the use of multiple tools. These present methods often require more than one person and large periods of time, leaving room for an increase in efficiency of the task of detecting and addressing FOD.

BRIEF DESCRIPTION OF THE DRAWINGS

To assist in understanding the present disclosure, reference is now made to the following description taken in conjunction with the accompanying drawings, in which.

DETAILED DESCRIPTION

To facilitate a better understanding of the present disclosure, the following examples of certain embodiments are given. The following examples are not to be read to limit or define the scope of the disclosure. Embodiments of the present disclosure and its advantages are best understood by referring to FIGS. 1 through 5, where like numbers are used to indicate like and corresponding parts.

As described, foreign object debris (FOD) may be present in an aircraft. It may be difficult to detect and/or remove the FOD from the aircraft to prevent potential damage. Described herein are various systems and methods that provide an improvement in detection, removal, sealing, and combinations thereof by using an inspection system.

Figure 1:
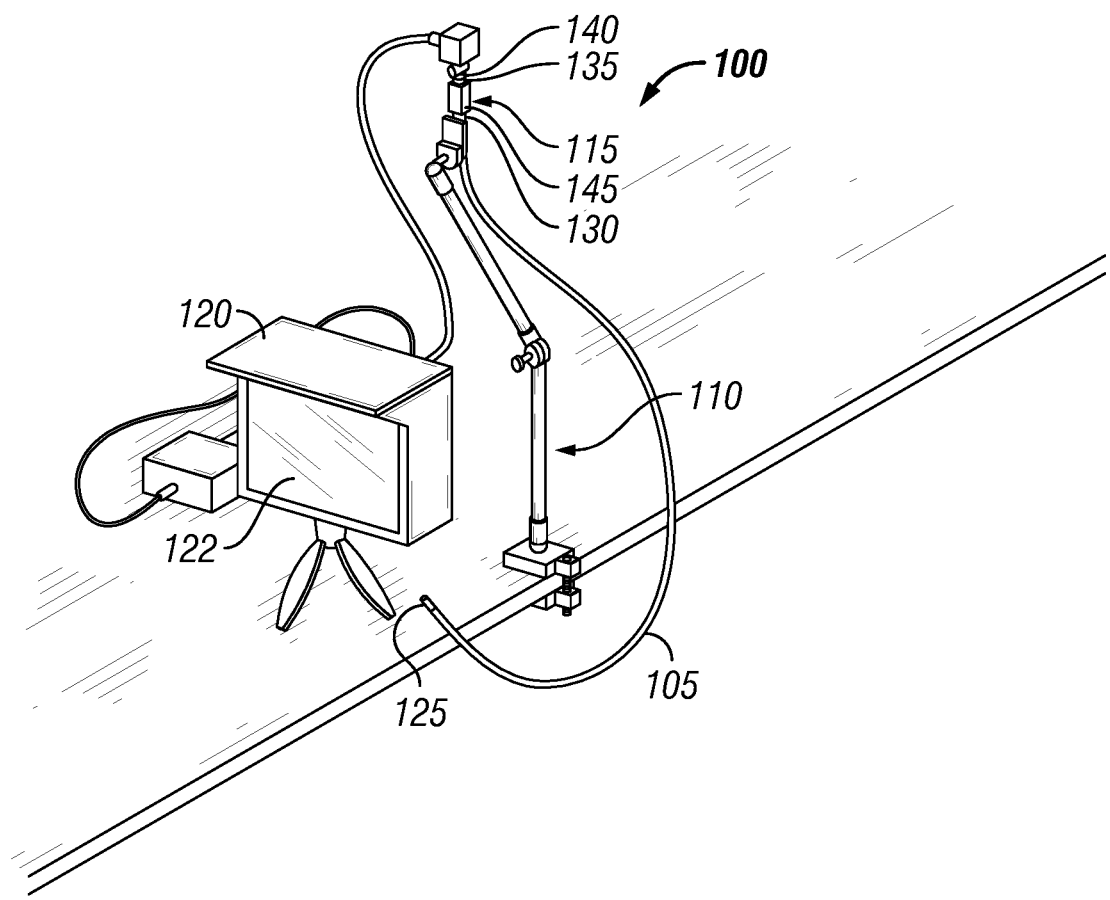
FIG. 1 illustrates an example inspection system, according to certain embodiments.

FIG. 1 illustrates an isometric view of an inspection system 100. The inspection system 100 may be configured to determine the presence of any FOD in an aircraft, to remove the FOD, to seal the FOD in place, and any combination thereof. In embodiments, the inspection system 100 may comprise a borescope 105, a mounting system 110, an articulation system 115, and a controller 120. In one or more embodiments, the borescope 105 may be configured to maneuver about and around areas that are small and/or difficult to access. The borescope 105 may be any suitable size, height, shape, and combinations thereof. In embodiments, the borescope 105 may comprise a tubular, wherein the tubular has an elongated, cylindrical shape. The borescope 105 may comprise any suitable materials. Without limitations, the suitable materials may be metals, nonmetals, polymers, composites, and any combinations thereof. In embodiments, the borescope 100 may be rigid, flexible, or a combination thereof. In certain embodiments, a portion of the borescope 105 may be flexible while the remaining portion of the borescope may be rigid. In one or more embodiments, the borescope 105 may further comprise an optical device, such as a camera (for example, camera 210 in FIG. 2), and a plurality of optical fibers. In these embodiments, the plurality of optical fibers may be disposed within the tubular and may connect a distal end 125 of the borescope 105 to the controller 120, wherein the optical device may be disposed at the distal end 125 of the borescope 105.

As illustrated, a proximal end 130 of the borescope 105 may be coupled to the mounting system 110. In embodiments, the mounting system 110 may be configured to secure the inspection system 100 to an external surface. Without limitations, the mounting system 110 may comprise any suitable components, such as tubulars, rods, clamps, hinges, fasteners, and the like. In embodiments, the mounting system 110 may be adjustable to secure the inspection system 100 at any suitable distance and/or angle to the external surface. The mounting system 110 may be any suitable size, height, shape, and combinations thereof. The mounting system 110 may further comprise any suitable materials. Without limitations, the suitable materials may be metals, nonmetals, polymers, composites, and any combinations thereof. In embodiments, the mounting system 110 may be coupled to the articulation system 115.

The articulation system 115 may be configured to actuate the borescope 105. In one or more embodiments, the articulation system 115 may comprise a first rotating lever 135, a second rotating lever 140, and a handle 145. The first rotating lever 135 may be configured to actuate a portion of the borescope 105 about the distal end 125 to bend along a horizontal plane with respect to the distal end 125. In embodiments, the second rotating lever 140 may be configured to actuate the portion of the borescope 105 about the distal end 125 to bend along a vertical plane with respect to the distal end 125. In one or more embodiments, the portion of the borescope 105 about the distal end 125 may have any suitable length necessary to operate in small areas within or about an aircraft. Without limitations, the length of the portion of the borescope 105 about the distal end 125 may be from about 1 inch to about 3 inches, from about 3 inches to about 5 inches, from about 5 inches to about 10 inches, and any combination thereof. In embodiments, the portion of the borescope 105 about the distal end 125 may have a length of about 5 inches. The portion of the borescope 105 about the distal end 125 may bend to form no greater than about a 120° angle with reference to the initial position of the distal end 125. Without limitations, the portion of the borescope 105 about the distal end 125 may form an angle of about 0.5° to about 45°, about 45° to about 90°, about 90° to about 120°, or any combination thereof with the initial position of the distal end.

In one or more embodiments, the first rotating lever 135 and/or the second rotating lever 140 may be actuated manually or automatically via the controller 120. In embodiments, the first rotating lever 135 and the second rotating lever 140 may be actuated to move the portion of the borescope 105 about the distal end 125 at the same time and/or at different times. The first rotating lever 135 and the second rotating lever 140 may be any suitable size, height, shape, and combinations thereof. In embodiments, the first rotating lever 135 and the second rotating lever 140 may have the same dimensions. In other embodiments, the first rotating lever 135 and the second rotating lever 140 may have different dimensions.

In one or more embodiments, the first rotating lever 135 and the second rotating lever 140 may be disposed adjacent to the handle 145. In these embodiments, the proximal end 130 of the borescope 105 may be attached to the handle 145, and the first rotating lever 135 and the second rotating lever 140 may be disposed at an opposite side of the handle 145 from the proximal end 130. In embodiments, the handle 145 may be configured to be physically manipulated by an operator when operating the inspection system 100. The handle 145 may be any suitable size, height, shape, and combinations thereof. The handle 145 may comprise any suitable materials. Without limitations, the suitable materials may be metals, nonmetals, polymers, composites, and any combinations thereof.

As illustrated, the handle 145 may be communicatively coupled to the controller 120. In one or more embodiments, the controller 120 may be configured to operate the inspection system 100 or individual components within the inspection system 100. During operations the controller 120 may control the movement and operation of the borescope 105. In one or more embodiments, the controller 120 may include one or more interface(s), processing circuitry, memory(ies), and/or other suitable element(s). In embodiments, an interface receives input, sends output, processes the input and/or output, and/or performs other suitable operation. Interface may comprise hardware and/or software. In embodiments, the controller 120 may further comprise a display 122, wherein the display 122 may be configured to display information obtained by the inspection system 100 to an operator, and wherein the operator may be able to control certain functions of the inspection system 100 through the display 122. Without limitations, the operator may take pictures or record video, control the lights disposed about the borescope 105 (for example, lights 205 in FIG. 2), access stored pictures and/or videos, control connectivity to a communication network, and any combinations thereof through the display 122.

Processing circuitry performs or manages the operations of the component. Processing circuitry may include hardware and/or software. Examples of a processing circuitry include one or more computers, one or more microprocessors, one or more applications, etc. In certain embodiments, processing circuitry executes logic (e.g., instructions) to perform actions (e.g., operations), such as generating output from input. The logic executed by processing circuitry may be encoded in one or more tangible, non-transitory computer readable media (such as memory). For example, the logic may comprise a computer program, software, computer executable instructions, and/or instructions capable of being executed by a computer. In particular embodiments, the operations of the embodiments may be performed by one or more computer readable media storing, embodied with, and/or encoded with a computer program and/or having a stored and/or an encoded computer program.

Memory (or memory unit) stores information. Memory may comprise one or more non-transitory, tangible, computer-readable, and/or computer-executable storage media. Examples of memory include computer memory (for example, RAM or ROM), mass storage media (for example, a hard disk), removable storage media (for example, a Compact Disk (CD) or a Digital Video Disk (DVD)), database and/or network storage (for example, a server), and/or other computer-readable medium.

Herein, a computer-readable non-transitory storage medium or media may include one or more semiconductor-based or other integrated circuits (ICs) (such field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Figure 2:
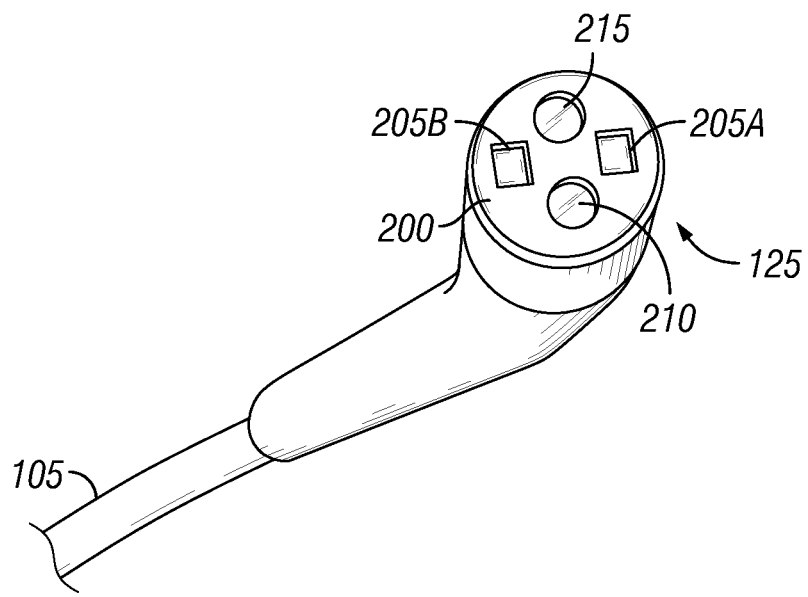
FIG. 2 illustrates an example distal end of a borescope of the inspection system in FIG. 1, according to certain embodiments.

FIG. 2 illustrates an embodiment of the distal end 125 of the borescope 105. As illustrated, a cover plate 200 may be disposed at the distal end 125. The cover plate 200 may seal the interior of the borescope 105 and secure further components at the distal end 125. The cover plate 200 may be any suitable size, height, shape, and configurations thereof. In embodiments, the cover plate 200 may have a circular cross-section having a diameter slightly larger than the outer diameter of the borescope 105, wherein there is at least a 1% to about a 5% tolerance between the cover plate 200 and the borescope 105. Without limitations, the cover plate 200 may be attached to the distal end 125 by any suitable means, including suitable fasteners, adhesives, threading, welding, brazing, and any combination thereof.

As illustrated, the cover plate 200 may comprise a first light 205A, a second light 205B (wherein both the first light 205A and the second light 205B will herein be referred to collectively as the lights 205), a camera 210, and a working channel 215. In embodiments, any suitable lights may be used for lights 205. In one or more embodiments, the lights 205 may be configured to project and supply light to a designated area for inspection via the borescope 105. In embodiments, the lights 205 may be any suitable size, height, shape, and combinations thereof. As illustrated, both the first light 205A and the second light 205B may be disposed in the cover plate 200. In certain embodiments, there may be at least one of the lights 205 disposed in the cover plate 200. The first light 205A and/or the second light 205B may be disposed about any suitable location and configuration in the cover plate 200. As illustrated, the first light 205A and the second light 205B may generally be disposed about opposite portions of the cover plate 200. In embodiments, the lights 205 may be electrically coupled to the controller 120 (referring to FIG. 1) through the use of any suitable wiring, wherein the wiring may be disposed within the interior of the borescope 105.

The camera 210 may be disposed in the cover plate 200 near the lights 205. In embodiments, the camera 210 may be disposed about any suitable location in the cover plate 200. As illustrated, the camera 210 may generally be disposed between the lights 205 but offset by a certain distance. In embodiments, the camera 210 may be any suitable size, height, shape, and combinations thereof. In embodiments, any suitable camera may be used for camera 210. In one or more embodiments, the camera 210 may be configured to record, capture, visually display, and combinations thereof information within a designated area for inspection via the borescope 105. In embodiments, the camera 210 may be electrically coupled to the controller 120 through the use of any suitable wiring (for example, fiber optic cables), wherein the wiring may be disposed within the interior of the borescope 105. During operations, as the camera 210 operates, the display 122 (referring to FIG. 1) may visually display information, images, video, and the like to an operator. In one or more embodiments, the operator may further utilize the working channel 215 to address any potential FOD discovered by the camera 210.

As illustrated, the working channel 215 may be disposed in the cover plate 200 near the lights 205. In embodiments, the working channel 215 may be disposed about any suitable location in the cover plate 200. As illustrated, the working channel 215 may generally be disposed between the lights 205 but offset by a certain distance and opposite to the camera 210. In other embodiments, the working channel 215 may be disposed about a center of the cover plate 200, and the lights 205 and/or camera 210 may be disposed in a suitable configuration around the working channel 215. In embodiments, the working channel 215 may be any suitable size, height, shape, and combinations thereof. As illustrated, the working channel 215 may have a circular cross-section. In one or more embodiments, the cross-section of the working channel 215 may be uniform along its length. In alternate embodiments, the cross-section of the working channel 215 may vary along its length. In embodiments, the working channel 215 may be a hollow channel running the length of the borescope 105. Without limitations, the working channel 215 may be configured to allow for a tool or component to be introduced through the handle 145 (referring to FIG. 1) for operation at or near the distal end 125 of the borescope 105. In other embodiments, the working channel 215 may provide a flow path from a designated area near the distal end 125, through the borescope 105, and to the handle 145.

Figure 3:
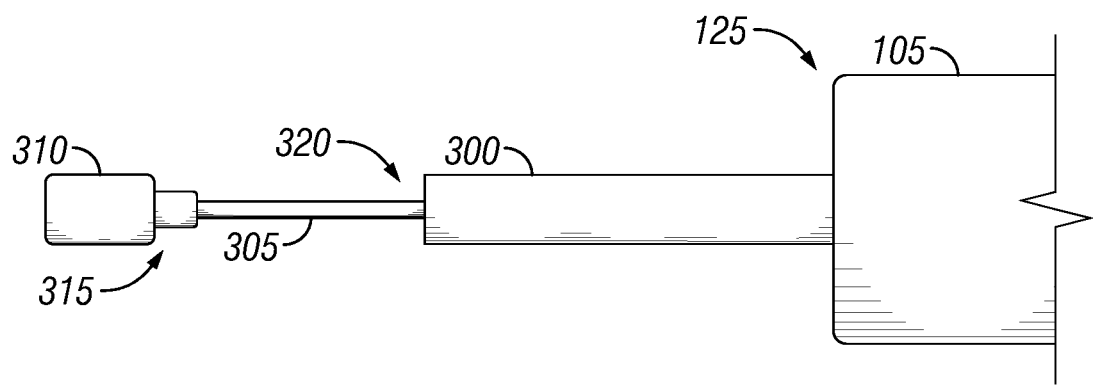
FIG. 3 illustrates an example distal end of a borescope of the inspection system in FIG. 1, according to certain embodiments.

FIG. 3 illustrates an embodiment of the distal end 125 of the borescope 105 in operation. In one or more embodiments, a tubular 300 may be disposed within the working channel 215 (referring to FIG. 2) of the borescope 105. In these embodiments, the tubular 300 may line the interior of the length of the working channel 215. The tubular 300 may be any suitable size, height, shape, and combinations thereof. The tubular 300 may also comprise any suitable materials. Without limitations, the suitable materials may be metals, nonmetals, polymers, composites, and any combinations thereof. In one or more embodiments, heat shrinking material, such as polyolefin, may be used for the tubular 300. In other embodiments, polyethylene and other similar polymers may be used for the tubular 300. In embodiments, a piston plunger 305 may be disposed within the tubular 300.

The piston plunger 305 may comprise a piston head 310 disposed at a distal end 315 of the piston plunger 305. The piston plunger 305 and the piston head 310 may be any suitable size, height, shape, and combinations thereof. In one or more embodiments, the piston head 310 may generally have the same diameter as the inner circumference of the tubular 300. The piston plunger 305 and the piston head 310 may also comprise any suitable materials. Without limitations, the suitable materials may be metals, nonmetals, polymers, composites, and any combinations thereof. In embodiments, the piston plunger 305 may be configured to translate the piston head 310 through and out of the tubular 300. During operations, a sealant (not shown) may be disposed within a distal portion of the tubular 300. In embodiments, the piston plunger 305 may be operated to translate or displace the piston head 310 towards and into the sealant to force the sealant to dispense from a distal end 320 of the tubular 300. The combination of the piston plunger 305 and the sealant may be used to seal any potential FOD into place in a designated area when an operator is not able to remove the FOD.

Figure 4:
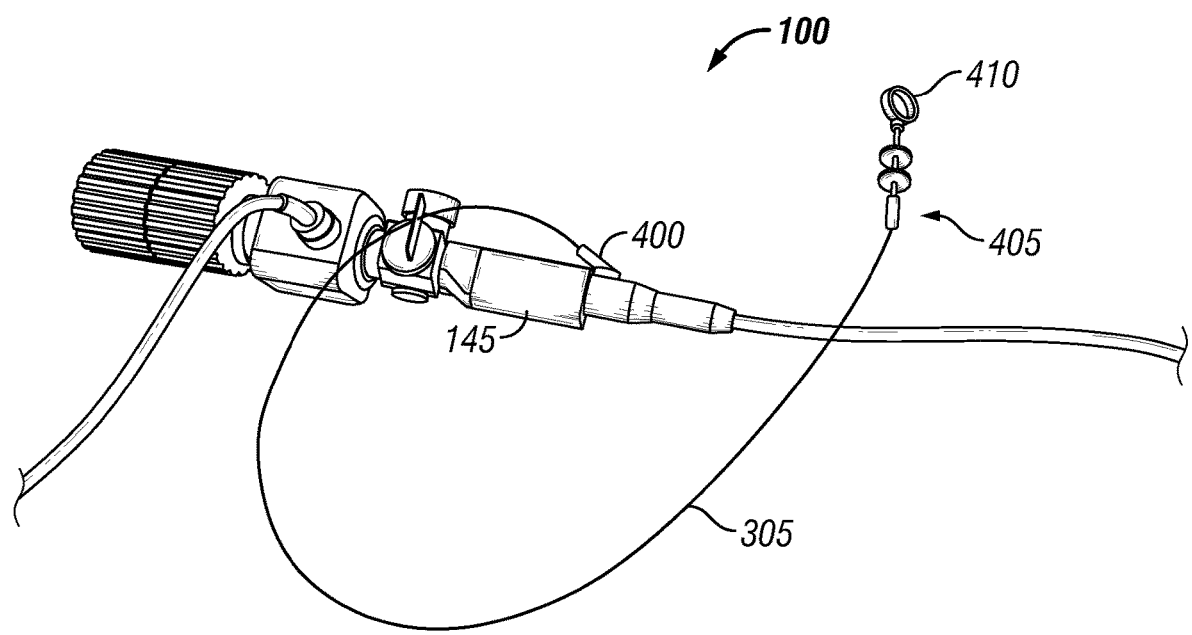
FIG. 4 illustrates an example inspection system, according to certain embodiments.

FIG. 4 illustrates an embodiment of the inspection system 100 with the piston plunger 305. As illustrated, the handle 145 may comprise a port 400, wherein the port 400 may provide access to the working channel 215 (referring to FIG. 2). In one or more embodiments, the piston plunger 305 may be introduced into the working channel 215 through the port 400. During operations, an operator may insert the distal end 315 (referring to FIG. 3) of the piston plunger 305 into the port 400 and feed the length of the piston plunger 305 through the working channel 215. In embodiments, a portion of the length of the piston plunger 305, up to the maximum at a proximal end 405 of the piston plunger 305, may be disposed into the working channel 215. As illustrated, a knob 410 may be disposed at the proximal end 405 of the piston plunger 305 for use by the operator. The knob 410 may be used to push and/or pull on the piston plunger 305 to translate or displace the piston head 310 (referring to FIG. 3) an equivalent distance. Without limitations, while it is illustrated that the piston plunger 305 may be inserted into the working channel 215, any other suitable tools may be used with the working channel 215. In embodiments, a mechanical and/or magnetic tool used to physically obtain FOD may be inserted into and through the working channel 215. In other embodiments, a measuring tool may be inserted into and through the working channel 215.

With reference to FIGS. 2-4, during operations, an operator may insert the piston plunger 305 into the working channel 215 through the port 400 and at least partially out of the cover plate 200. In embodiments, the tubular 300 may be disposed over and around at least a portion of the piston plunger 305. Without limitations, heat may be applied to the tubular 300 so as to heat shrink the tubular 300 to the piston plunger 305. In embodiments, any suitable method of applying heat to the tubular 300 may be used, such as, but not limited to, a hot air gun. The operator may retract the piston plunger 305 with the tubular 300 back into and through the working channel 215 so that the tubular 300 may line at least a portion of the interior of the working channel 215. In one or more embodiments, a sealant may be injected into the distal end 320 of the tubular 300. Without limitations, any suitable sealant may be used. In embodiments, the sealant may be thick and/or viscous. Once the sealant is disposed within a portion of the tubular 300, the operator may displace the piston plunger 305 through the working channel 215, thereby dispensing the sealant onto any potential FOD in a designated area. In embodiments, the FOD may be completely encapsulated by the sealant and may be fixed to its present location. In other embodiments, the sealant may at least partially cover the FOD as long as it is fixed to its present location. In one or more embodiments, the operator manually actuates the piston plunger 305. In other embodiments, actuation of the piston plunger 305 may be automatic through the controller 120 (referring to FIG. 1).

Figure 5:
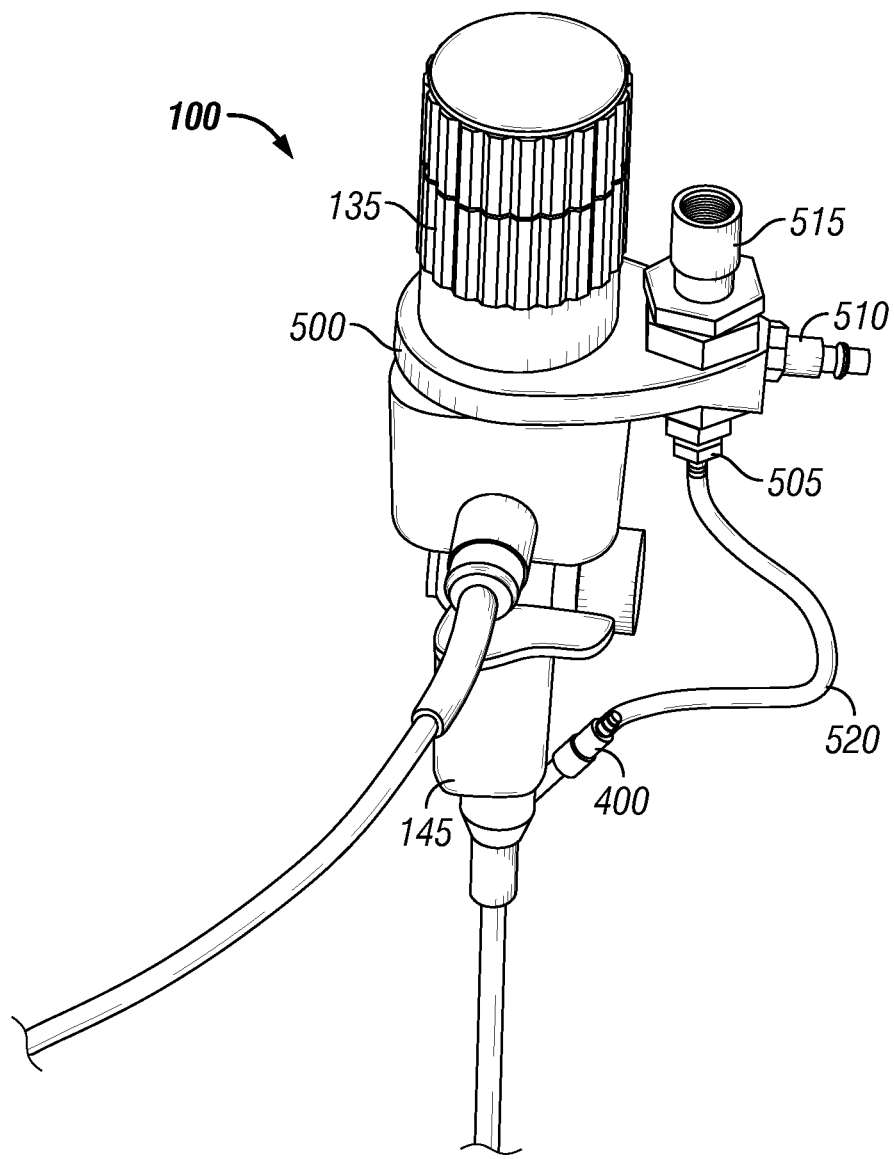
FIG. 5 illustrates an example inspection system, according to certain embodiments.

FIG. 5 illustrates an embodiment of the inspection system 100 with a vacuum attachment 500. As illustrated, a vacuum attachment 500 may be disposed between the handle 145 and the first rotating lever 135. The vacuum attachment 500 may be configured to couple a means of vacuuming (for example, an air supply) to the inspection system 100, wherein the inspection system 100 may be capable of vacuuming any potential FOD in a designated area through the borescope 105. The vacuum attachment 500 may be any suitable size, height, shape, and combinations thereof. The vacuum attachment 500 may also comprise any suitable materials. Without limitations, the suitable materials may be metals, nonmetals, polymers, composites, and any combinations thereof.

As illustrated, the vacuum attachment 500 may comprise a port coupling 505, an air supply coupling 510, and a containment coupling 515. The port coupling 505 may be configured to indirectly couple the port 400 to the vacuum attachment 500. In embodiments, a conduit 520 may be attached to both the port 400 and the port coupling 505 so as to couple the port 400 to the port coupling 505. The port coupling 505 may be disposed on a bottom surface of the vacuum attachment 500. In embodiments, the containment coupling 515 may be disposed on a top surface of the vacuum attachment 500. The containment coupling 515 may be configured to couple an external container (not shown) to the vacuum attachment 500, wherein the external container may receive any potential FOD being removed from a designated area with the means of vacuuming. The air supply coupling 510 may be disposed on a side surface of the vacuum attachment 500. The air supply coupling 510 may be configured to couple any suitable air supply to the inspection system 100 through the vacuum attachment 500. In one or more embodiments, any suitable and/or standard coupling may be used for any of the port coupling 505, the air supply coupling 510, and the containment coupling 515. In embodiments, while the port coupling 505, the air supply coupling 510, and the containment coupling 515 are illustrated in a certain configuration in FIG. 5, each of the port coupling 505, the air supply coupling 510, and the containment coupling 515 may be disposed at any suitable location about the vacuum attachment 500. Without limitations, each of the port coupling 505, the air supply coupling 510, and the containment coupling 515 may be a male or female coupling.

Technical advantages of this disclosure may include one or more of the following. The inspection system 100 described herein may reduce the amount of time and/or tooling required to inspect a designated area, remove FOD, seal FOD, and any combination thereof. The borescope 105 may be configured to access hard to reach areas about an aircraft and may be capable of addressing any potential FOD through either means of vacuuming, sealing, mechanically and/or magnetically grabbing, and any combination thereof while the borescope 105 remains in position.

The present disclosure may provide numerous advantages, such as the various technical advantages that have been described with respective to various embodiments and examples disclosed herein. Other technical advantages will be readily apparent to one skilled in the art from the following figures, descriptions, and claims. Moreover, while specific advantages have been enumerated in this disclosure, various embodiments may include all, some, or none of the enumerated advantages.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method of operating an inspection system, comprising:
    lining a working channel of at least a portion of a borescope with a tubular;
    inserting at least the portion of the borescope about a distal end of the borescope into a designated area;
    actuating the borescope through a means of a rotating lever;
    displaying a location of foreign object debris through a camera disposed at the distal end of the borescope;
    translating a piston plunger through a portion of the tubular lining the working channel, wherein the piston plunger exits the tubular at the distal end of the borescope; and
    dispensing a sealant onto the foreign object debris by displacing the sealant from the tubular using the piston plunger to fix the foreign object debris to the location.

2. The method of claim 1, further comprising injecting the sealant into tubular at the distal end of the borescope.

3. The method of claim 1, wherein dispensing the sealant onto the foreign object debris comprises automatically dispensing the sealant onto the foreign object debris.

* * * * *